United States Patent [19]

Korth et al.

[11] Patent Number: 5,196,011
[45] Date of Patent: Mar. 23, 1993

[54] CUTTING ELECTRODE FOR MEDICAL RESECTOSCOPE

[75] Inventors: Knut Korth, Merzhausen; Bernd Nösel, Lutjensee, both of Fed. Rep. of Germany

[73] Assignee: Olympus Winter & Ibe GmbH, Hamburg, Fed. Rep. of Germany

[21] Appl. No.: 756,335

[22] Filed: Sep. 6, 1991

[30] Foreign Application Priority Data

Oct. 15, 1990 [DE] Fed. Rep. of Germany ....... 4032601

[51] Int. Cl.⁵ .............................................. A61B 17/39
[52] U.S. Cl. ...................................................... 606/46
[58] Field of Search ...................................... 606/45, 46

[56] References Cited

U.S. PATENT DOCUMENTS 5,080,660 1/1992 Buelna .............................. 606/46 X Primary Examiner—Lee S. Cohen
Attorney, Agent, or Firm—Walter C. Farley

[57] ABSTRACT

A cutting electrode for medical resectoscope has an insulated loop support displaceable in the axial direction of the resectoscope shaft, the distal end of the support carrrying an un-insulated cutting loop extending from the end of the loop support transversely to the axial direction a predetermined distance depending on the extent of cutting desired. A spacer carried by the loop support extends distally in front of the cutting loop and laterally of the cutting loop a smaller distance than that of the cutting loop and is shaped to provide smooth, low-friction engagement with tissues with which it comes in contact.

7 Claims, 3 Drawing Sheets

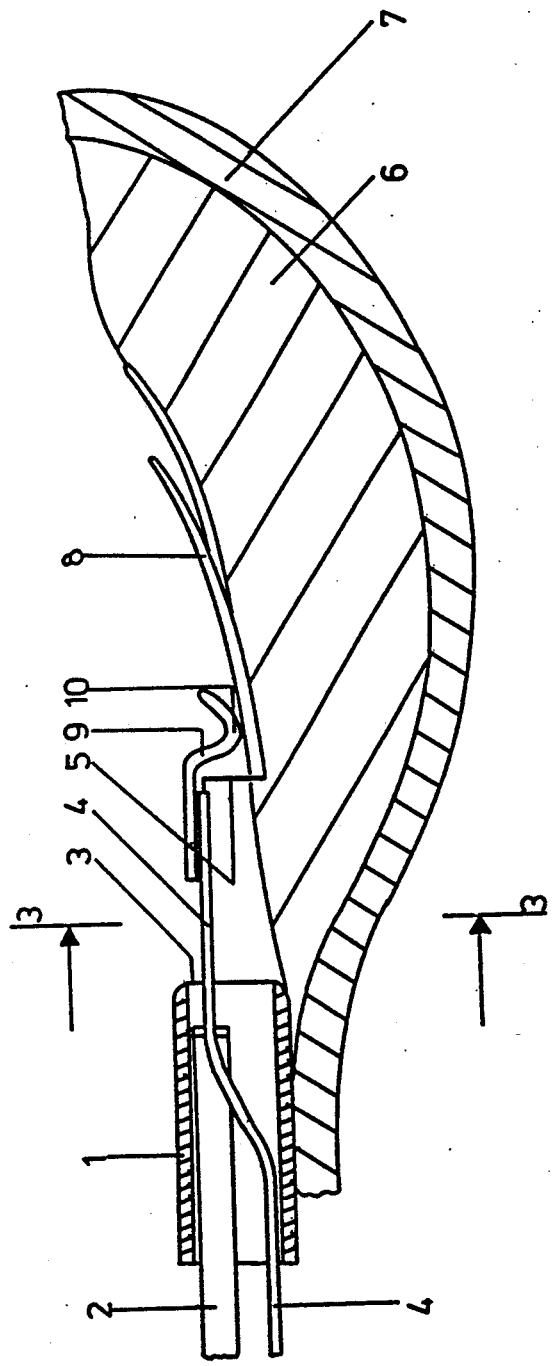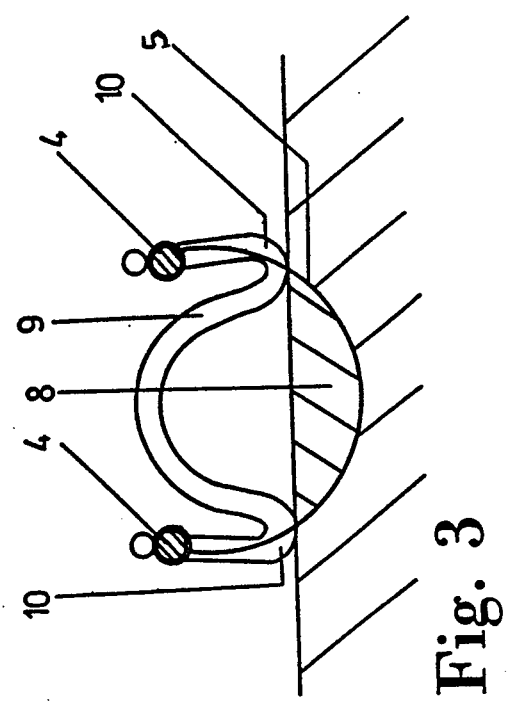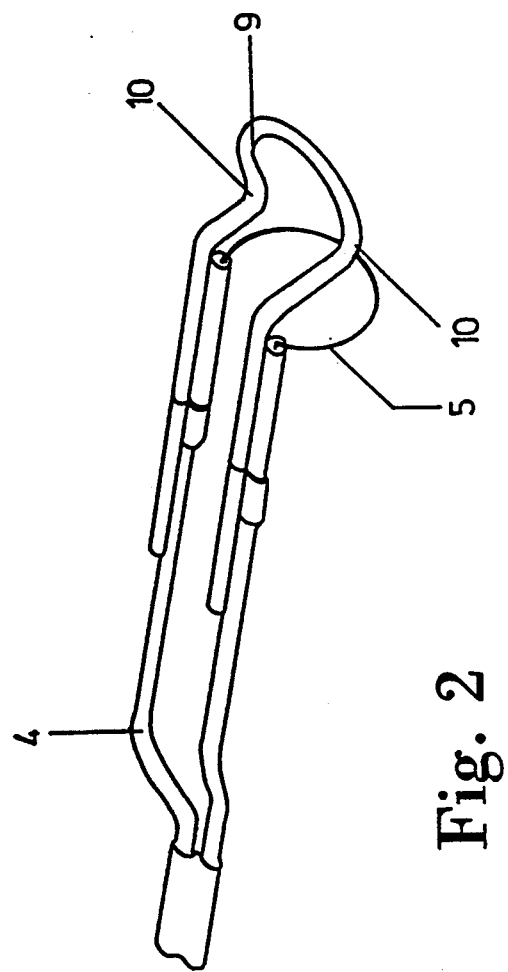

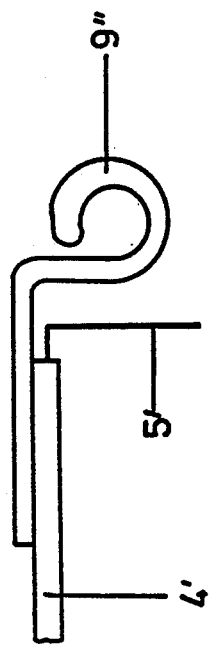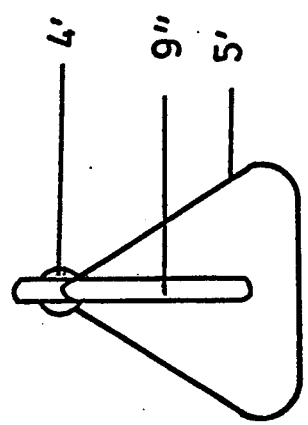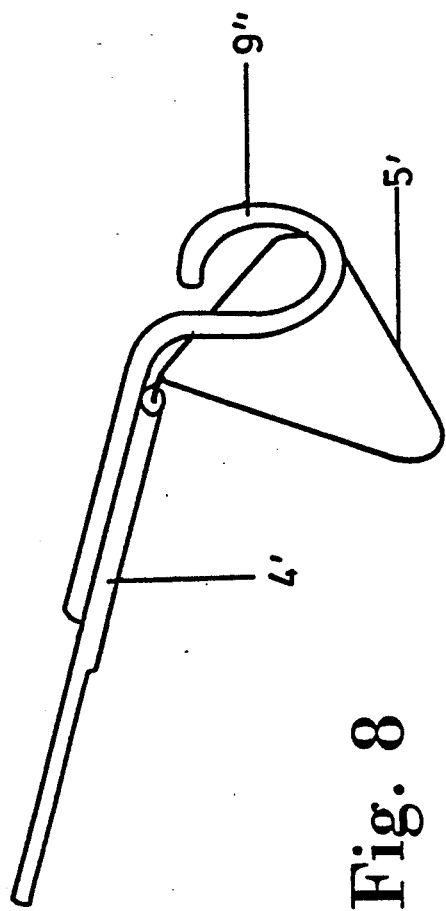
Fig. 7
Fig. 9
Fig. 8

CUTTING ELECTRODE FOR MEDICAL RESECTOSCOPE

FIELD OF THE INVENTION

This invention relates to a cutting electrode for a medical resectoscope.

BACKGROUND OF THE INVENTION

Cutting electrodes are used in medicine to remove tissue, typically in urology and, in that field, especially for purposes of prostate resection. The cutting electrode is connected to a high-frequency generator which is turned ON or OFF by the surgeon by actuating a switch. When the high frequency is on, the cutting loop very easily and almost without encountering resistance cuts through the body tissue. However, certain drawbacks accompany the easy, nearly effortless cutting with such an electrode. The surgeon is required to concentrate on the surgery and always must know precisely how deeply he may cut. Unplanned motion or faulty estimation of the desired safe depth of cut lead to unwanted injury to the patient.

In the conventional electrode drive design, such a cutting electrode, when in the rest position, is inside the tubular shaft of the resectoscope. It may be advanced from the distal shaft end to the front where it can be moved to-and-fro. With the high-frequency power turned ON, cutting can be accomplished by moving the electrode with its cutting loop forward and back. In the immediate vicinity of the resectoscope shaft, the possible cutting depth is inherently limited by how the shaft rests. However, the more the loop moves away from the shaft, the deeper the possible cut, and the greater the risk of cutting excessively deeply. Moreover, there is danger of cutting too much forward, i.e., in the direction away from the shaft.

SUMMARY OF THE INVENTION

An object of the present invention is to create a cutting electrode for medical resectoscope that allows greater safety.

This object is achieved by providing an electrode having an insulated loop support displaceable axially to and from the resectoscope shaft, the distal end of the loop support carrying an un-insulated cutting loop extending transversely from the end of the loop support to a selected depth which determines the maximum cutting depth, and including a spacer which extends distally in front of the cutting loop and downward to a lesser distance than the loop.

The cutting electrode of the invention comprises an insulated, that is a non-cutting spacer mounted ahead of the loop, that is, it subtends forward spacing and prevents unwanted forward penetration. The spacer also projects somewhat downward to a location where it can rest on the tissue surface, whereby the cutting loop can only make an incision having a depth corresponding to the amount by which its depth exceeds that of the spacer. Accordingly, the main dangers of unwanted cutting forward and unduly deep cutting downward are excluded or at least restricted. Such an electrode allows proceeding rapidly even with diminished concentration or poor visibility, danger of injury to patient being largely excluded. The cutting electrode of the invention therefore protects against erroneous incisions caused by unintended motions by the surgeon. Similarly the cutting electrode of the invention also protects against erroneous cuts due to involuntary motions of the patient. A known instance in urology is nervus obturatorius, which may be stimulated when working in the bladder and then leads to reflexive motion by the patient, in the course of which unwanted contact between tissue and cutting loop arises.

Making the spacer as an insulated wire bail is desirable because manufacture is economical, the bail being able in a simple manner to assume a wide variety of arbitrary geometries.

Because of the runner-like design of the parts of the spacer resting on the tissue, sliding is easy, so that cutting is unhampered.

Providing a roller on the spacer is advantageous because good sliding is achieved with rolling rest.

A stable, two-point electrode rest is achieved by forming the bail with two low points, enhancing cutting accuracy. Moreover the rest points thereby are located to the side of the incision made by the electrode, as a result of which this electrode cannot affect this reliable rest.

Shaping the bail so that it curves upwardly between the lowest points does not impede the surgeon's clear forward view between loop and wire bail.

BRIEF DESCRIPTION OF THE DRAWINGS

In order to impart full understanding of the manner in which these and other objects are attained in accordance with the invention, a particularly advantageous embodiment thereof will be described with reference to the accompanying drawings, which form a part of this disclosure, and wherein:

FIG. 1 is a side elevation in section of the lower half of a prostate showing the resectoscope in cutting readiness;

FIG. 2 is a perspective view of the electrode of FIG. 1;

FIG. 3 is an enlarged transverse sectional view along line 3—3 of FIG. 1;

FIG. 7 is a side elevation of a third embodiment of an electrode in accordance with the invention;

FIG. 8 is a perspective view of the electrode of FIG. 7; and

FIG. 9 is an axial end elevation of the embodiment of FIGS. 7 and 8.

DESCRIPTION OF THE PREFERRED EMBODIMENTS

Figures 4, 5:
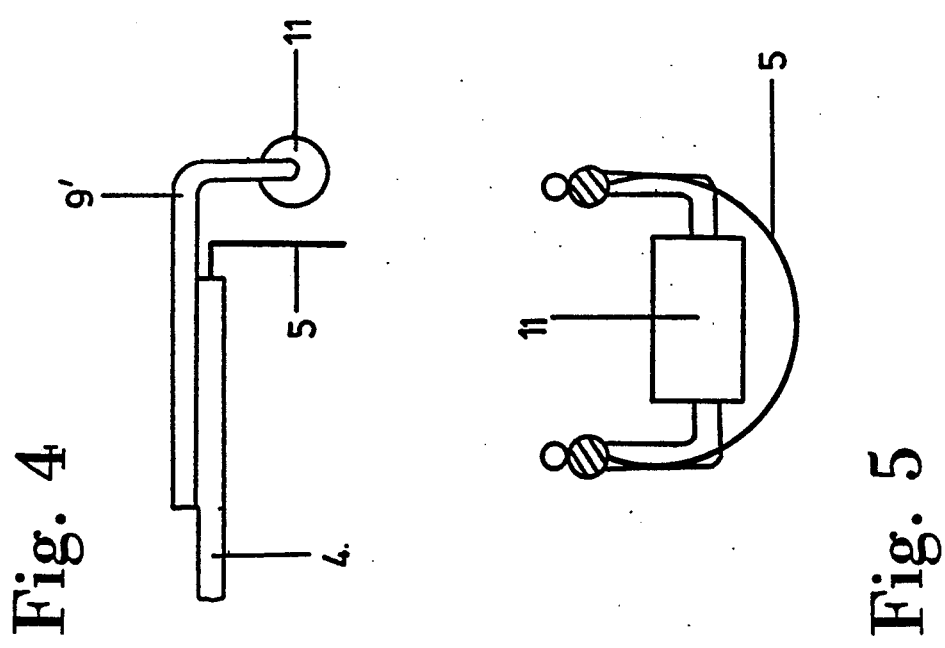
FIG. 4 is a side elevation of a second embodiment of an electrode in accordance with the invention.
FIG. 5 is an end elevation similar to that of FIG. 3 of the electrode of FIG. 4.

FIG. 1 is a longitudinal section of the distal end of the shaft 1 of a resectoscope. An optical viewing tube 2 is mounted in the shaft and looks forward (in the distal direction) though the open end of the shaft bounded by the rim 3. Moreover, a cutting electrode is mounted in the shaft and includes a loop support 4 with a cutting loop 5.

A conventional, commercial cutting electrode is shown, the longer part of the support including a rod forking toward the distal end and comprising a semi-circularly bent cutting loop 5 between the fork tine ends. The cutting loop 5 consists of un-insulated wire. The remainder of the loop support 4 is insulated externally.

When high-frequency power is applied to the loop, cutting takes place at the cutting loop 5, the electrical circuit typically being completed through the body of the patient.

The loop support 4 is movable to-and-fro in the axial direction of the resectoscope shaft 1. As a rule, cutting takes place with the shaft 1 fixed in position and with the electrode being moved to-and-fro, hf power being applied. Ordinarily the work is done backward as shown in FIG. 1 which shows the resectoscope in a prostate with prostate tissue 6 to be removed inside a sheath 7 which must not be injured.

The electrode design described so far is employed as shown in FIG. 1. With a retracting motion, a tissue strip 8 is cut off as shown by FIG. 3.

The depth of cutting must be adjusted precisely by tilting the shaft 1 to the proper angle relative to the tissue to be incised. Because the cutting loop 5 cuts very easily, almost effortlessly, through tissue, cutting may be inadvertently too deep. Especially when the surgeon reaches the point at which much of the prostate tissue 6 has been removed and cutting takes place near the sheath 7, it is possible to accidentally cut into this sheath.

The danger is especially large when cutting forward, in extension of the shaft 1, and cutting too far, so to injure the patient this way, for instance by perforating the sheath 7.

The structure of the invention prevents such occurrences by providing a spacer which in the embodiment shown is a wire guard or bail 9. Illustratively, the wire bail 9 comprises a metal wire externally insulated and affixed at opposite sides to opposite tines of the loop support 4 by, for instance, being glued or welded to it. As shown by FIGS. 1 through 3, the bail projects forward beyond the cutting loop 5 and then its sides are bent laterally, down to a depth somewhat less than the depth of the cutting loop 5. At the positions denoted by 10, the wire bail bends upward and forwardly somewhat like the end of a sled runner or ski tip. As shown in FIG. 1, this runner portion of the wire bail 9 rests on the tissue, allowing easy, friction-free sliding on the tissue surface.

FIGS. 1 and 3 show the manner in which the runner-shaped rest points of wire bail 9 rest on the tissue surface as a result of which the cutting depth of the cutting loop 5 is automatically limited, the cutting loop being unable to penetrate deeper than the difference in downward extension between the cutting electrode and the bail as shown in the Figures. Even with a somewhat distracted surgeon, the cutting loop 5 cannot penetrate deeper. This limit on cutting depth applies both to backward and to forward resection.

The wire bail 9 also establishes forward spacing. If any body part is touched in the forward direction, the contact is by means of the non-cutting wire bail 9, and accidental injury will thus be avoided.

As shown in FIGS. 1 through 3 and especially by FIG. 3, the wire bail 9 is formed with an upward bend between the lowest bend points, or locations of greatest distance from the loop support, at 10. The surgeon looking through the optical viewer 2 in the axial direction of the shaft will see the cutting loop 5 and the wire bail 9 approximately in the manner shown by FIG. 3. Because the center of the distal end of the wire bail 9 is bent upward, the surgeon enjoys a clear field of view between the cutting loop 5 and the wire bail 9, especially even when these components are directly in front of the optics 2 in the case of a rearward cutting electrode.

FIG. 3 also shows that the separation of the locations 10 of greatest separation of the spacer from the loop support are spaced from each other about the same distance as the ends of the cutting loop.

Figure 6:
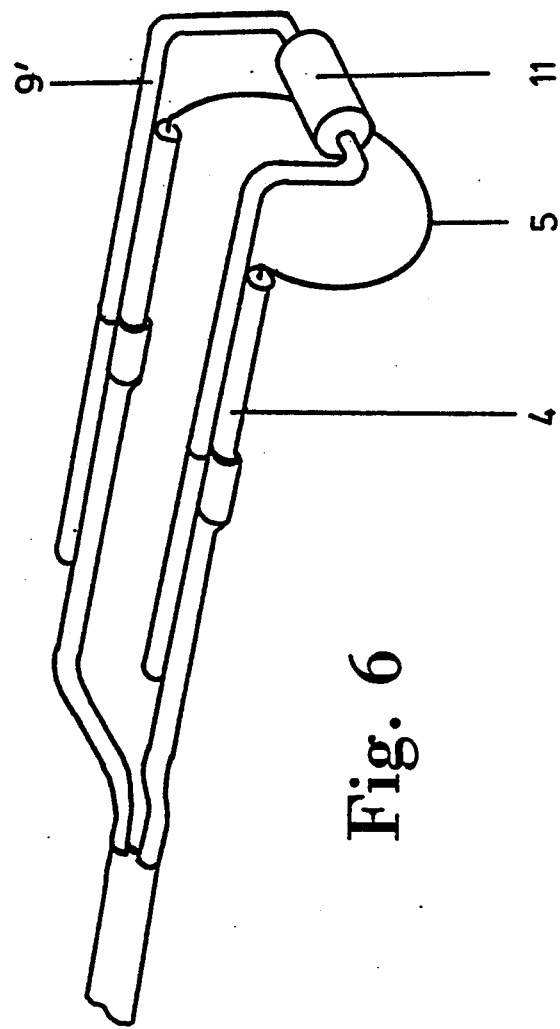
FIG. 6 is a perspective view of the electrode of FIGS. 4 and 5.

FIGS. 4 through 6 show a second embodiment of a cutting electrode in accordance with the invention wherein the loop support 4 and the cutting loop 5 are similar to those elements as shown in FIGS. 1 through 3. Again, the spacer consists of a wire bail 9'. However, bail 9' at its lowest point has a straight section which forms an arbor for a roller 11. This roller rests in a rolling manner on the surface of the tissue being cut, for instance the prostate tissue 6 of FIG. 1, and also allows easy, friction-free cutting with reliable limitation on depth and forward motion.

FIGS. 7 through 9 show a third embodiment wherein another loop support 4' is used, which is not forked in its distal zone and which supports a closed cutting loop 5' of a somewhat different shape. In accordance with the invention, a wire bail 9'' extends forward along an extension of the central axis of the loop support and downwardly therefrom. The bail 9'' is formed into a loop which, again, is like a runner at its lowest point.

However, the cutting loop embodiment shown in FIGS. 7 through 9 can also be provided with a wire bail carried by the loop support 4' which is of simple design, the bail being of a shape corresponding to that shown in FIGS. 1 through 3 or else fitted with a roller as in FIGS. 4 through 6. The wire-bail designs 9, 9', 9'' shown in the Figures may consist of insulated metal wires, though also of suitably resistant, particularly heat-resistant, plastic. The spacer furthermore may be designed to be a suitably shaped, spatially closed body.

Cutting loops differing in shape from those shown in the Figures may be equipped in matching manner with spacer for which it is important in each case that they shall extend distally in front the cutting loop and down part of the cutting loop depth. The lowest points of each such spacer, by which it can rest on the tissue, is preferably easily slidable on the tissue surface, that is, for instance being made like runners as shown in FIGS. 1 through 3 and further in FIGS. 7 through 9, or else being equipped with a roller as shown in FIGS. 4 through 6.

In a variation of the embodiment shown in FIGS. 1 through 3, the wire bail 9 also may be centrally split and consist of two parts, each forming a runner.

The purpose of the spacer in the above described embodiment is to isolate the cutting loop in the forward direction and further to limit the cutting depth. However, the spacer also may project sideways beyond the cutting loop and prevent thereby the cutting loop from laterally touching body parts.

The limitation of the cutting depth of the cutting electrodes shown results in restricting the resection speed. Accordingly, at the beginning of surgery, when substantial volumes must be removed, a conventional cutting electrode without a spacer may be employed. This conventional electrode then may be exchanged for a cutting electrode of the invention to carry out the last fine work near organs not to be touched, such as in the case of prostate resection, when removing the last remainders of the prostate tissue 6 from the surface of the sheath 7 without cutting into the sheath itself. Cutting electrodes of the invention may be made available to the surgeon in assortments with varying cutting depths.

The invention also is applicable to cutting electrodes revolving about the axis of the shaft and for which the cutting loop essentially is located in a plane passing through this shaft axis. In this case again a spacer would be provided which projects as far as in front of the cutting loop and further so far downward, i.e., in annular or lamellar form towards all sides starting from the axis of rotation, such that consequently the cutting depth of the rotating loop shall be limited thereby.

What is claimed is:

1. A cutting electrode structure for a medical resectoscope of the type having a hollow shaft having a central axis, the electrode comprising
   an electrically insulated loop support displaceable axially with respect to the resectoscope shaft, said loop support having proximal and distal ends;
   an un-insulated, electrically conductive cutting loop carried by said distal end of said loop support and extending laterally a predetermined distance from said loop support;
   a spacer (9, 9', 9'') carried by said loop support (4, 4'), said spacer extending distally beyond said cutting loop (5, 5') and extending laterally in the same direction as said cutting loop but a smaller distance from said loop support, thereby limiting the cutting depth of said loop.

2. A cutting electrode according to claim 1 wherein said spacer (9, 9', 9'') is an insulated wire bail.

3. A cutting electrode according to claim 2 wherein said spacer is bent to form zones (10) of maximum distance from said loop support, said zones (10) of the spacer (9) being shaped in the form of sliding runners.

4. A cutting electrode according to claim 2 wherein said support has a longitudinal axis and including a roller (11) with a central axis supported on said spacer, said central axis of said roller extending transversely to said longitudinal axis of said support, said roller being on a portion of said spacer at a maximum distance from said loop support.

5. A cutting electrode according to claim 2 wherein said cutting loop (5) has a predetermined width and wherein said wire bail (9) comprises two locations (10) of greatest separation from said loop support, said locations being laterally spaced apart from each other by a distance substantially corresponding to said width of said cutting loop (5).

6. A cutting electrode according to claim 5 wherein said wire bail (9) curves inwardly between said locations of greatest separation.

7. A cutting electrode according to claim 1 wherein said spacer is formed with zones (10) of maximum distance from said loop support, said zones (10) of said spacer (9) being shaped with distally extending curves in the form of sliding runners.

* * * * *